(12) United States Patent
Hamill

(10) Patent No.: US 6,491,653 B1
(45) Date of Patent: Dec. 10, 2002

(54) HAMILL SPLINT

(76) Inventor: Barry M. Hamill, 6543 E. Wilson St., Fountain, NC (US) 27829

( * ) Notice: Subject to any disclaimer, the term of this patent is extended or adjusted under 35 U.S.C. 154(b) by 0 days.

(21) Appl. No.: 09/812,050

(22) Filed: Mar. 19, 2001

(51) Int. Cl.[7] ................................................ A61F 5/00

(52) U.S. Cl. ............................................ 602/5; 602/21

(58) Field of Search .................................. 128/846, 869, 128/877, 878, 879; 602/5, 20, 21, 22, 23, 60, 61, 62, 63, 64

(56) References Cited

U.S. PATENT DOCUMENTS

| | | | | |
|---|---|---|---|---|
| 1,512,558 A | * | 10/1924 | Montgomery | 602/6 X |
| 2,506,464 A | * | 5/1950 | Millheisler | 602/6 |
| 3,232,289 A | * | 2/1966 | Zimmerman | 602/6 |
| 4,029,090 A | * | 6/1977 | Dawson | 128/88 |

* cited by examiner

*Primary Examiner*—Michael A. Brown
(74) *Attorney, Agent, or Firm*—Joseph N. Breaux

(57) ABSTRACT

A splint for immobilizing the arm of a patient prior to transporting the patient to a site for further medical treatment. The splint includes a number of adjustable length arms which can be locked in fixed positions with thumbscrews.

1 Claim, 2 Drawing Sheets

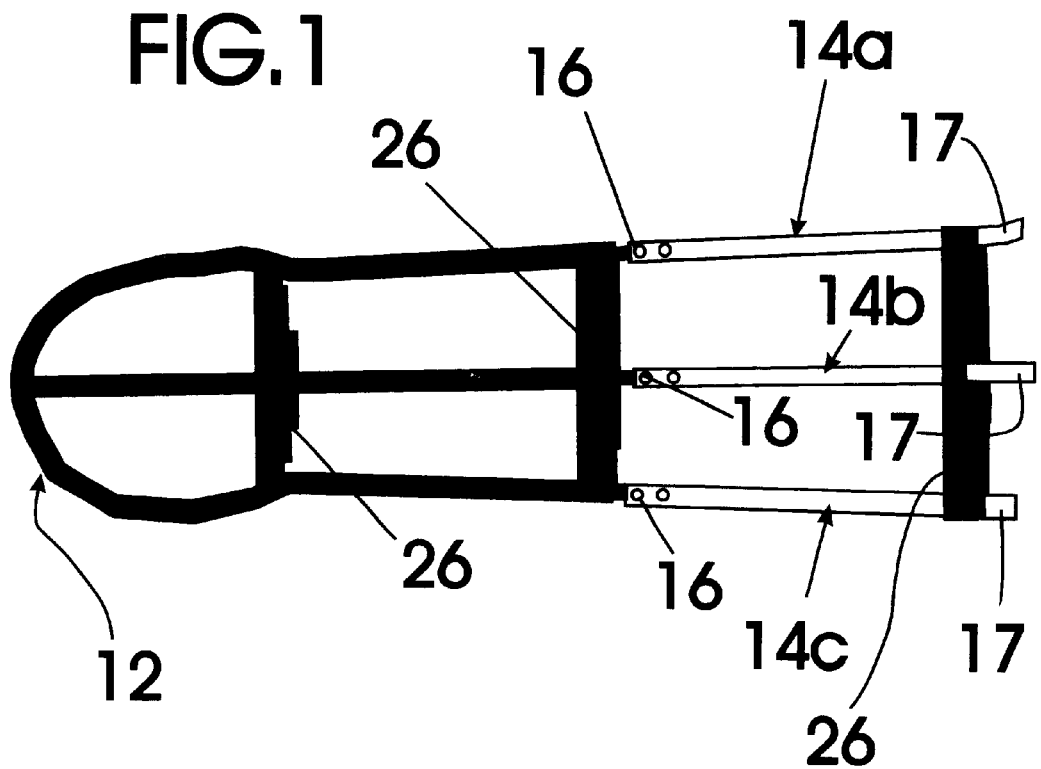
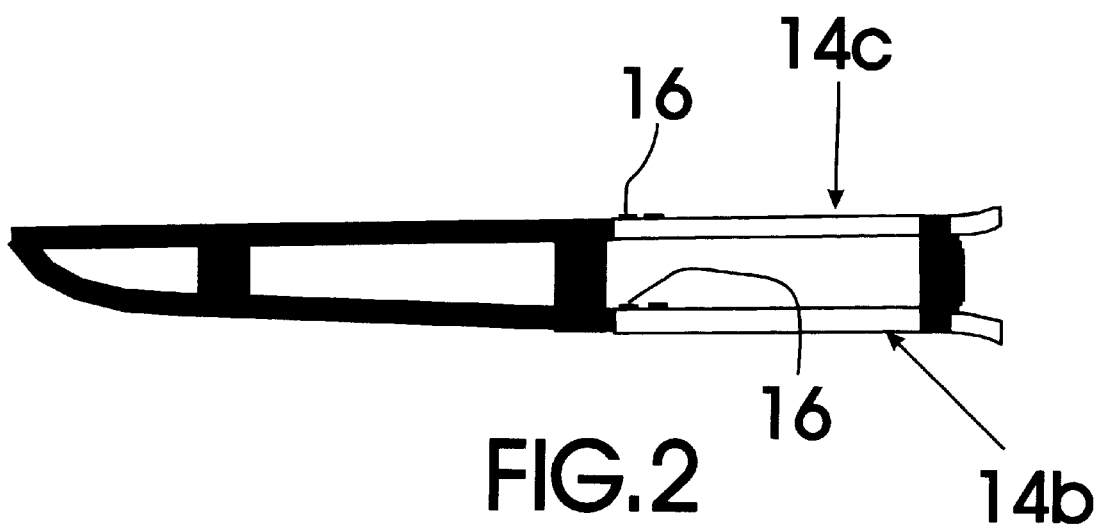

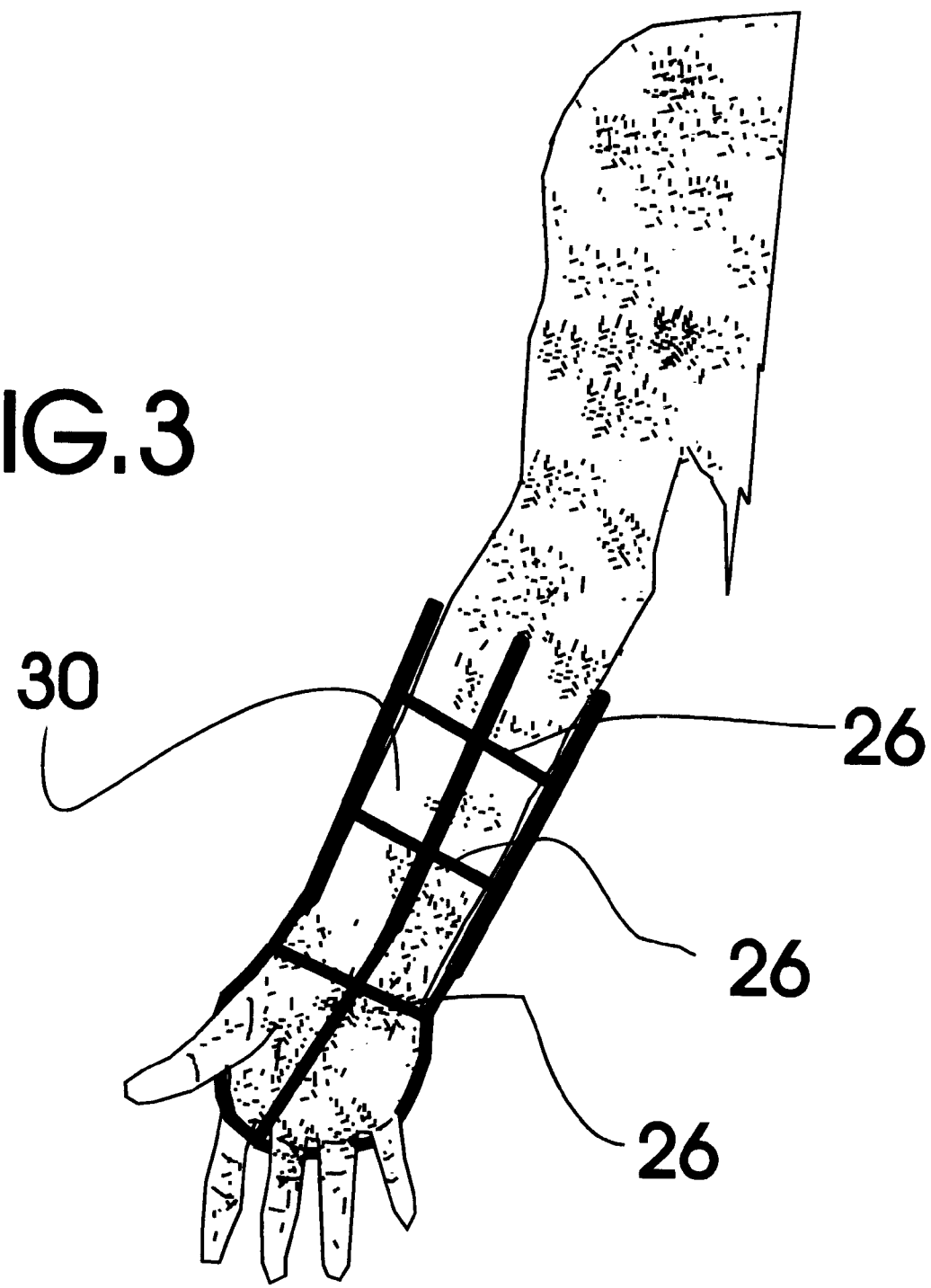

HAMILL SPLINT

TECHNICAL FIELD

The present invention relates to medical equipment and more particularly splints applied to broken or fractured arms.

BACKGROUND OF INVENTION

It is often necessary to immobilize a broken or fracture bone in an arm or the like prior to transporting a patient to a site where further medical treatment can be performed. It would be a benefit, therefore, to have a splint which could be easily and rapidly attached to a limb suspected of having a broken or fractured bone. Because movement of the limb when applying the splint can further aggravate any injuries, it would be a further benefit if the splint could be applied to the patient's limb in a manner that would not require substantial movement of the limb.

SUMMARY OF INVENTION

It is thus an object of the invention to provide a Hamill splint for immobilizing a limb suspected of having a broken or fractured bone. The splint is easily and rapidly attached to the limb to immobilize the limb for transport to a medical treatment facility. It is further an object of the invention to provide a splint which can be applied to a limb suspected of having a broken or fractured bone that did not require substantial movement of the arm to apply.

Accordingly, a Hamill splint is provided that has round or curved head and three extending support arms. Each of the support arms is telescopic in design and fixable in length by an incorporated thumbscrew on each arm. The end of each arm is flared to prevent the end from scratching or pinching the flesh of the user. The center support arm is off set (lower) from the other arm creating a central cradle for the limb of the user. Velcro straps are provided to secure the splint to the arm. As an option the splint could be available in different sized or adjustable middle support arm to adjust to the left and right arms. Finger clips could also be provided to secure the fingers to immobilize them if necessary. A hand cushion could also be provided in the hand area if so desired.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein:

FIG. 1 shows a top view of the Hamill splint of the present invention.

FIG. 2 shows a side view of the Hamill splint of the present invention.

FIG. 3 shows the Hamill splint applied to the arm and hand area of a representative arm and hand.

EXEMPLARY EMBODIMENTS

FIG. 1 shows a top view of the Hamill splint of the present invention generally designated 10. Hamill splint 10 includes a curved head generally designated 12 and three telescopic arms generally designated 14a, 14b, 14c which are adjustable in length and each terminated in a flared end 17 which prevents the end of the arm from digging into the limb of the patient during use, and are securable at a desired length with thumbscrew 16. The center support arm 14b is positioned in a different plane than and between the other two support arms 14a and 14c to create a cavity for holding the limb to be supported. A number of adjustable length Velcro straps 26 are provided between arms 14a and 14c to secure the splint in place during use around wrist and arm area 30 of a user. It can be seen from the preceding description that a Hamill splint has been provided. seen from the preceding description that a Hamill splint has been provided.

It is noted that the embodiment of the Hamill splint described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A splint device for splinting arms and hands suspected of having broken bones; the splint device comprising:

a curved head portion formed at the rigid forward convergence connection of three arm supports;

each said arm support being adjustable in length and lockable at a desired length with a thumb screw locking mechanism;

said three arm supports including a center arm support that is positioned in a different plane than and between the other two arm supports in a manner such that a cavity for holding the arm to be supported is created;

a number of adjustable length hook and pile fastener securable straps are provided that are each secured to the center support arm and around the other support arms in a manner to secure the support arms to an arm positioned within the cavity and to hold the arm securely in place during use;

each said arm support terminating at an end opposite the curved head portion in a flared end that are flared such that the flared end is oriented away the cavity and from an arm supported by said splint device within said cavity.

* * * * *